US009517297B2

(12) United States Patent
Almohizea

(10) Patent No.: US 9,517,297 B2
(45) Date of Patent: Dec. 13, 2016

(54) APPARATUS AND METHOD FOR TRANSDERMAL DELIVERY OF BIOACTIVE SOLUTION

(71) Applicant: King Saud University, Riyadh (SA)

(72) Inventor: Saad Ibrahim Almohizea, Riyadh (SA)

(73) Assignee: King Saud University, Riyadh (SA)

( * ) Notice: Subject to any disclaimer, the term of this patent is extended or adjusted under 35 U.S.C. 154(b) by 571 days.

(21) Appl. No.: 13/668,813

(22) Filed: Nov. 5, 2012

(65) Prior Publication Data
US 2013/0150826 A1 Jun. 13, 2013

(30) Foreign Application Priority Data
Dec. 8, 2011 (EP) ..................................... 11192505

(51) Int. Cl.
*A61M 31/00* (2006.01)
*A61M 5/00* (2006.01)
*A61M 5/178* (2006.01)
*A61M 5/32* (2006.01)
*A61M 37/00* (2006.01)

(52) U.S. Cl.
CPC ................ *A61M 5/00* (2013.01); *A61M 5/178* (2013.01); *A61M 5/3295* (2013.01); *A61M 37/00* (2013.01); *A61M 5/3298* (2013.01)

(58) Field of Classification Search
CPC ............ A61M 5/00; A61M 2037/0023; A61M 2037/0046; A61M 2037/0061; A61M 5/3295; A61M 5/3298; A61M 37/0015; A61M 2037/003

USPC .................................................. 604/173, 506
See application file for complete search history.

(56) References Cited

U.S. PATENT DOCUMENTS

| 7,284,474 | B2 | 10/2007 | Eigemann et al. |
| 2005/0165358 | A1 | 7/2005 | Yeshurun et al. |
| 2009/0187167 | A1 | 7/2009 | Sexton et al. |
| 2010/0121307 | A1* | 5/2010 | Lockard et al. ............... 604/506 |
| 2010/0256594 | A1* | 10/2010 | Kimmell ........... A61M 37/0015 604/506 |

FOREIGN PATENT DOCUMENTS

| CN | 101670145 | 3/2010 |
| EP | 1695734 | 5/2002 |
| KR | 1020080100569 | 11/2008 |
| WO | 03/026732 | 4/2003 |
| WO | 2004/045671 | 6/2004 |
| WO | 2010/051551 | 5/2010 |

* cited by examiner

*Primary Examiner* — Edelmira Bosques
*Assistant Examiner* — Leah Swanson
(74) *Attorney, Agent, or Firm* — Renner, Otto, Boisselle & Sklar, LLP

(57) ABSTRACT

Apparatus for transdermal or subcutaneous delivery of a bioactive solution, including a plurality of needles fixed on a needle carrier in a spaced apart relationship and projecting from the needle carrier, each needle having a tip zone adapted to receive an amount of bioactive solution from a reservoir coupled to the needle carrier and to deliver the bioactive solution upon penetrating a skin.

5 Claims, 5 Drawing Sheets

APPARATUS AND METHOD FOR TRANSDERMAL DELIVERY OF BIOACTIVE SOLUTION

CROSS-REFERENCE TO RELATED APPLICATION

The present application claims priority under 35 U.S.C. §120 to European Application No. 11192505.3, filed 8 Dec. 2011, the entirety of which is incorporated herein by reference.

BACKGROUND

The present invention relates to an apparatus and a method for transdermal or subcutaneous delivery of a medical or bioactive solution.

Topical application, local or external, is the mainstay treatment in skin diseases because of its ease and reduced systemic side effects. However it has been shown in various studies that only 1% of the drug gets absorbed inside regardless of the vehicle used. The reason for that are that the skin is protected by keratinous dead layers that wards of germs and insulates the inner body from the outside environment. This means that more frequent applications or prolonged duration of treatment are needed to reach desired results. Furthermore most of the drug gets wasted without even reaching its target.

Another reason for the reduced efficacy of local or external treatment is the chance of it being rubbed off or removed by the patient or others. To bypass the outside barrier, occasionally intralesional injections are given. These are only given by trained medical personnel and requires experience to know the proper depth of treatment and is usually painful if many injections are needed. Another problem is that an injector can reach only a tiny part with each injection. If he is to treat the whole area he has either to inject large amounts of fluid per injection or introduce the needle many times before it dulls and hurts even more. Another problem is that even if an injector performs multiple injections it is hard to control the depth and the volume injected each time he injects. The last statement is especially true in curved surfaces. It would also take a long time to finish the treatment.

A method of treatment known as mesotherapy is routinely done in clinics to treat various skin diseases by injecting through an automated pulsating needle which is moved by the injector manually from one site to another as the needle emerges back and forth. The problem with such treatment is that the treatment doesn't take into account the changing topography of the skin with the treatment given at varying depths and it's impossible to correctly space the injections. Additionally only a tiny part of the skin gets treated each time. Since one of the main indications of mesotherapy is liposculpturing, injecting at various depths may predispose to irregularities later on.

Chemical peels are compounds used to exfoliate the skin in a controlled manner to treat various skin diseases. They include but are not restricted to trichloroacetic acid, phenol, glycolic and salicylic acid peels. After prepping the skin, the peel of choice is applied on the skin evenly with the use of gauzes in one or more coats until the end point is reached. The patient goes home anticipating the healing phase to last anywhere from days to weeks depending on the peel. During this healing phase, skin starts to peel off, and new skin formation takes place as the redness and oozing fades away. This phase is known as downtime period.

Aging skin is characterized by wrinkling, rough texture and uneven pigmentation. These characteristics are associated with decreased Elastin, collagen, epidermal atrophy, cellular atypia, and dysplasia. These changes presumably result from DNA mutation and other cellular and protein damage. The consequence is abnormal collagen, Elastin, and ground substance breakdown. Cumulative sun exposure and smoking are some of the causes of photodamaged skin.

The wounds created by these acids stimulate the skin to synthesize collagen and induce peeling of the epidermis leading to skin regeneration. The result is a healthier skin with improved texture, smoothening of wrinkles, tightening of skin and amelioration of pigmentary changes. Therefore chemical peels are used to treat signs of aging and photodamage such as wrinkles and precancerous lesions. It has also been used for various diseases such as melasma, acne, dyschromias, epidermal growths such as wart and milia.

Depending on the depth of these peels, they have been classified into superficial, medium and deep peels. When the peel extends to only the epidermis they are known as superficial peels. Whereas medium depth peels extend into upper reticular dermis and deep peels into mid reticular dermis. The type of the peel, its concentration, the duration of treatment and other factors determine the depth of the peel.

As with any medical procedure, chemical peels may be associated with complications. This is especially true with deep peels with all of the epidermis and a huge portion of the dermis damaged leaving the skin vulnerable during the healing phase. A common complication seen in phenolic deep peels is post inflammatory hypopigmentation. Scarring, post inflammatory hyperpigmentation, persistent erythema and delayed healing are other examples. Furthermore, since the deep peels produce deep oozing wounds, there is a higher rate for infection and a long downtime and the patient may wait weeks to months before he or she is completely healed.

Due to these complications, medium and deep peels, such as phenol and trichloroacetic acid 35% and higher are falling out of favour as the treatment of choice for skin rejuvenation. Therefore it would be desirable to have a method by which a peel's rejuvenating potential is maximized without significant complications and with less downtime. Another reason for the unpredictable results seen with chemical peels given in a traditional way is that the gauze that is used to apply the acid on the skin is applied with varying pressures depending on how firm is it applied and how much acid is left in the gauze before reapplication. This is different from one doctor and another and even in the same patient when curved surfaces such as the neck is met, making the treatment hard to standardize with the uneven application.

Dermarollers have been used to induce wounds that stimulate collagen deposition, but only have modest results since it is not accompanied by injecting materials into the skin. Some practitioners would apply the solutions onto the skin before using a dermaroller hoping that the needle would transfer the solution inside the skin but only a fraction of that reaches and only superficially in a non standardized way. Furthermore the holes induced by the dermaroller tend to close by coagulation limiting any spread of solution.

It would be desirable to have a device that tackles the above problems and can be used to deliver bioactive substances, drugs or cosmeceuticals to the skin uniformly.

According to the invention, the above mentioned problems are at least partially solved by an apparatus for transdermal or subcutaneous delivery of a bioactive solution, including a plurality of needles fixed on a needle carrier in a spaced apart relationship and projecting from the needle carrier, each needle having a tip zone adapted to receive an amount of bioactive solution from a reservoir coupled to the needle carrier and to deliver the bioactive solution upon penetrating a skin.

Advantageously, the tip zone is hollow. In some embodiments, the reservoir is pressurized. The problems of the invention are at least partially solved by a method of subcutaneously or transdermally delivering a bioactive solution, by using an apparatus according to the invention, applying or rolling the apparatus on the skin, thereby delivering an amount of solution each time a needle penetrates the skin. According to the invention, it is advantageous that the solution comprises at least one of the following substances: phenol, trichloroacetic acid, glycolic acid, salicylic acid, jessner's peel, aminolevulinic acid, methyl aminolevulinate, botox, corticosteroid, filler.

DETAILED DESCRIPTION

First Embodiment

Figure 1:
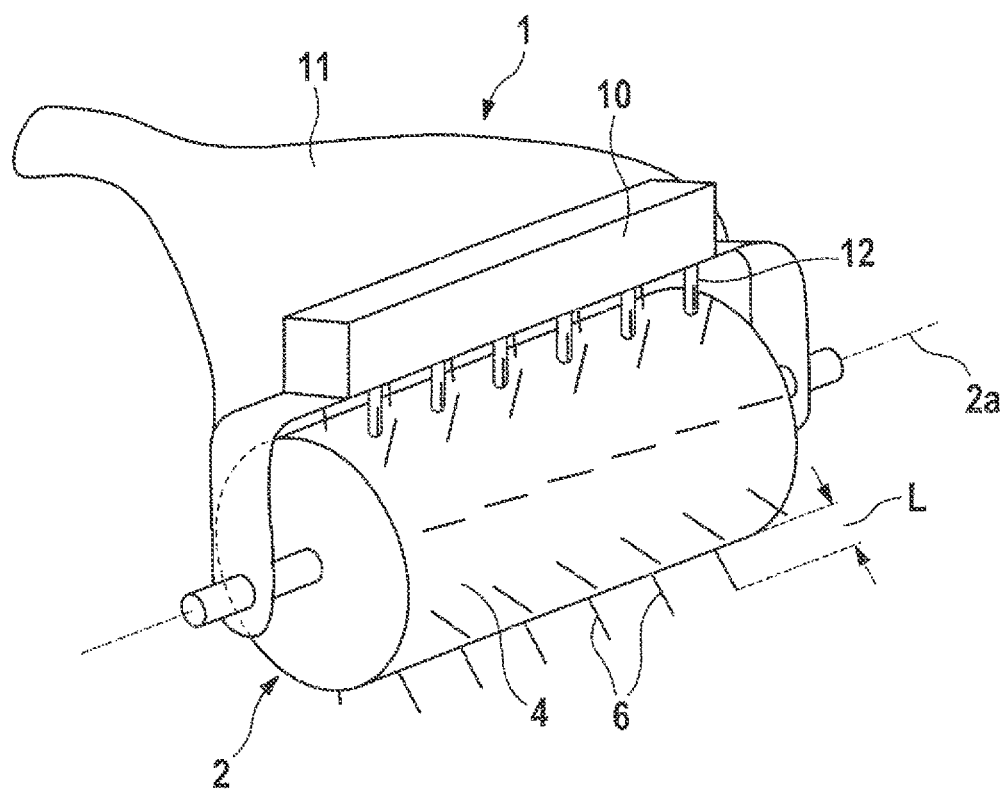
FIGS. 1 to 3 show various views of a first embodiment of the invention.

An apparatus 1 comprises a roller 2 that can be moved on the skin. About an outer surface 4 of the roller 2 is disposed a plurality of needles 6, preferably equidistant from each other. A length L of each needle 6 can be from 0.1 cm to 3 cm depending on the disease to be treated. Preferably, the needles point radially outwardly and perpendicularly from the surface 4 as shown in FIG. 1. As the roller rolls over the skin the needles smoothly in sequence puncture the skin and emerge out to complete a full circle before puncturing the skin again.

Figure 2:
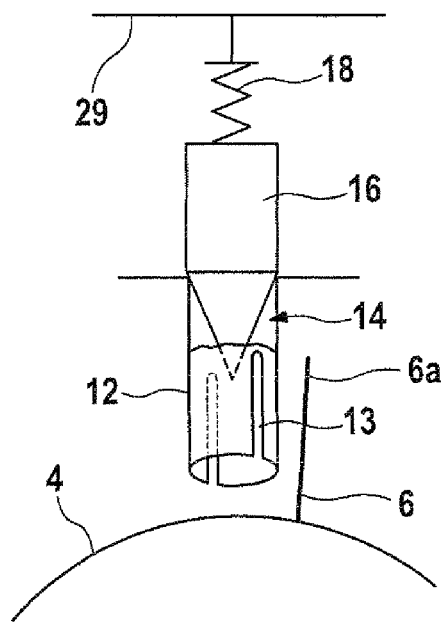
Figure 3:
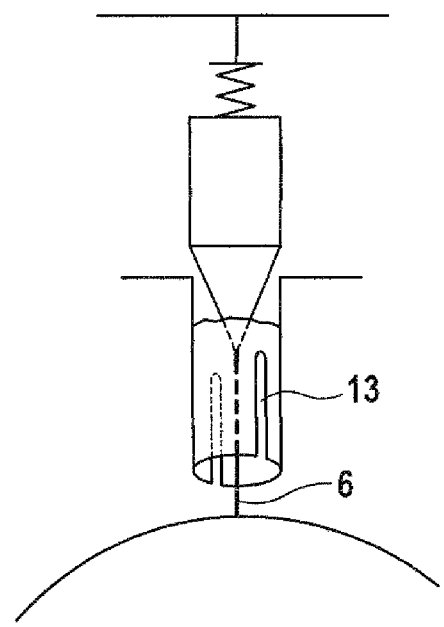

Arranged on top of the roller 2 is a compartment 10 that houses the bioactive material in form of a fluid or a solution to be delivered to the skin. Preferably, the compartment 10 is attached to a handle 11 that rotatably supports the roller 2 about an axis of rotation 2a. The compartment 10 in a bottom portion thereof has perforations 12 each of which is in form of hollow tubular portion and extends towards the roller 2. Each perforation 12 has cuts 13 at its sides to allow the moving needles 6 to pass within the perforations 12. At a resting phase (FIG. 2) an outlet device or outlet 14 of the perforation 12 is guarded by a slider 16 or gate element which is operatively connected to a spring 18. The spring 18 is anchored at a wall 29 of the compartment. As the needle 6 passes through its designated perforation 12 it moves the conically or triangularly shaped slider or gate element upwards (radially away from the roller 2), thus opening the outlet 14 and allowing only a predetermined volume of fluid to flow within the perforation 12. This volume depends on the indication and the area treated. For example the volume may range from about 0.01 ml to 0.3 ml for the purpose of skin rejuvenation in the face.

The needle 6 or at least a tip portion 6a which can be hollow or porous, gets wetted or soaked with the solution and delivers the solution as it turns further and punctures the skin on its way. Each time a needle completes a circle it gets soaked again with the fluid that gets dispensed with each rotation. The spring 18 assures that the slider 16 moves back to its resting and closing position once the needle has moved away. The diameter of the perforation should be tiny to hold the fluid within and prevent it from spilling down by gravity. A preferred inside diameter of a perforation is between 0.2 and 2 mm, preferably about 0.5 mm.

If desired, in a variation of the first embodiment a cleaning compartment can be installed adjacent the solution compartment 10, to contain cleaning solution and to clean the needles from blood and debris before they get soaked again with the solution. Normal saline can be used to clean the needles in the cleaning compartment. In an embodiment, a cleaning perforation is arranged similar to and next to each perforation 12, each cleaning perforation having an outlet and a gate element like the outlet 14 and the gate element 16, and is apt to deliver cleaning solution to each needle before the needle gets in contact with the perforation 12.

Second Embodiment

Figure 4:
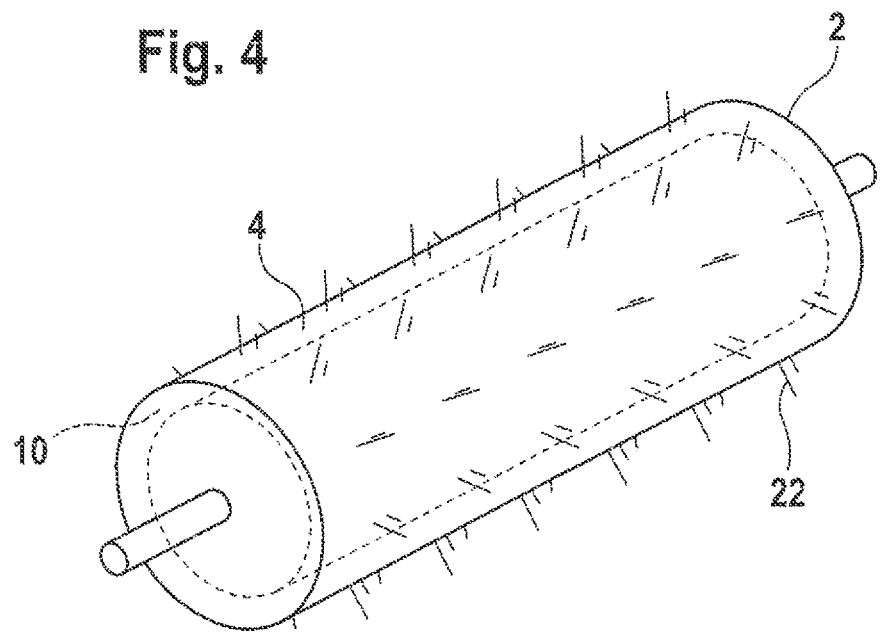
FIGS. 4 to 6 show various views of a second embodiment.
Figure 5:
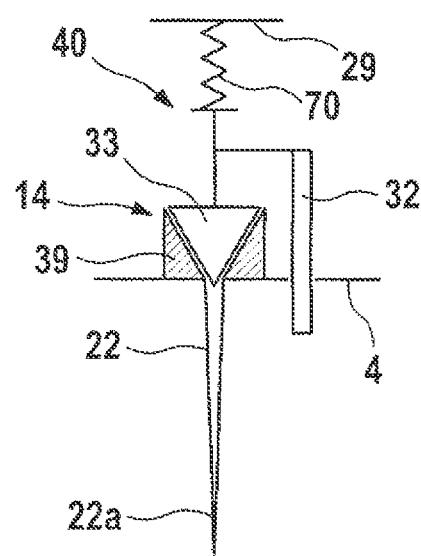
Figure 6:
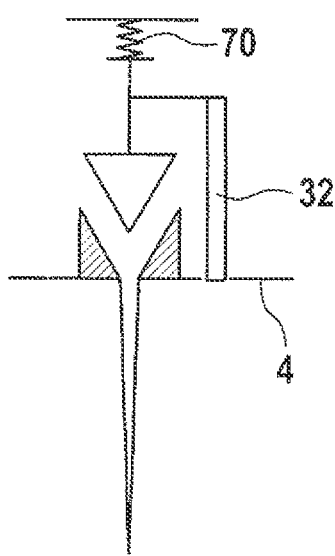

A roller 2 has multiple needles 22 mounted perpendicular on its outer surface 4 similar to the first embodiment as shown in FIG. 4 (handle not shown). Inside the roller is the solution or drug to be administered by the roller. It can only escape from the roller through outlets 14 and the needles. Each needle is internally hollow up to its tip 22a by virtue of a lumen and can communicate with the inside of the roller if a corresponding outlet is opened. The needle 22 is closed at a resting position by a gate element 40. The gate element is movable from a positing where the outlet is open and the solution can flow into the lumen of the needle (FIG. 6), to another position where the outlet is blocked by the gate element and no solution can flow (FIG. 5). The gate element has a conical or triangular head 33 that fits tightly into a seat 39 of complementary shape. At the other end the gate element is fixed at an inside wall 29 of the roller by a spring 70 arranged in between. Connected to the gate element is an arm 32 that extends outside the roller and acts as a contact element or switch. The arm protrudes perpendicularly from the roller and is in tight engagement with the outer surface of the roller to prevent fluid from spilling outwards. The arm is located close to the needle to coordinate the release of the gate element upon the needle's insertion into the skin. This is accomplished because the arm is operatively coupled to the spring and as it moves it also causes the gate element to slide back and forth.

In action, as the roller is passed onto the skin smoothly the needles eventually pierce the skin and progressively go deeper. Before a needle reaches its deepest level inside the skin, the arm comes into contact with the skin and gets displaced (FIG. 6), it gets pushed between the skin and the roller, this causes the arm to move inside the roller against the spring's resistance, with the gate also moving with it and the solution flows inside the needle and into the skin. The shape of the gate element and its seat (33 and 39) assures that the solution is forcefully delivered into the skin rather than remaining inside the needle because of resistance or pressure inside the skin. The shape and size of the engagement should be predetermined to deliver the desired volume of solution per stroke which should, range from about 0.1 ml to 3 ml which is enough to make a change but not a lot to cause problem in injecting under high pressures.

In a variation of the last embodiment the arm or switch can be doubled at either side of the needle or circular in shape with the needle at the centre to guarantee that the roller can be used in either direction. The length of the switch and the distance from the needle dictates when the solution gets dispelled. The spring's resistance should only be light to make rolling the device onto the skin smooth. If desired a sudden snap back mechanism at the spring can be used to aid in the injection phase.

Figure 9:
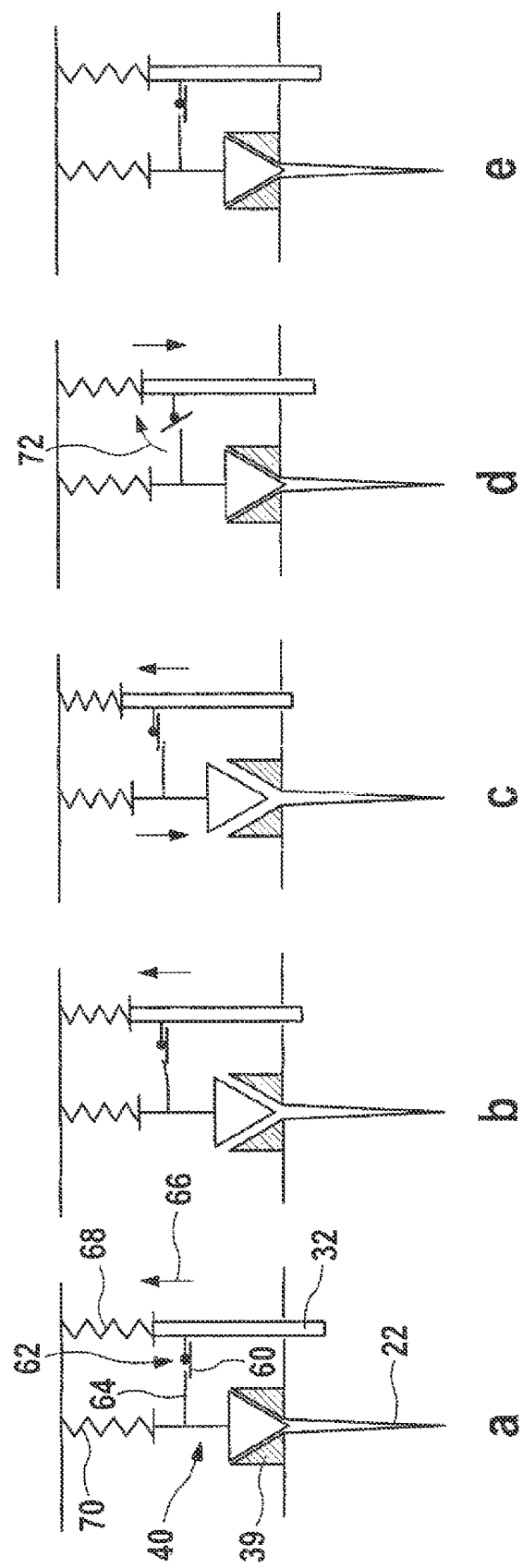
FIG. 9a to e illustrate a snap back mechanism usable in the fourth embodiment.

FIG. 9 shows an embodiment illustrating a ratchet and snap-back mechanism connecting the arm or contact element 32 with the gate element 40. The contact element 32 carries a pivotable lever 60. Lever 60 can rotate about pivot 62 in a clockwise direction, as seen in FIG. 9, starting from a position as in FIG. 9a. An elastic arm 64 is fixed to the gate element 40 and projects therefrom laterally. Upon intrusion of the needle 22 into the skin, the contact element 32 is moved into the roller (direction 66) against the force of a spring 68. The lever 60 is supported at a first end 60a by the contact element 32 against rotation and engages the elastic arm 64 with a free or second end 60b, thus lifting the gate element 40 from seat 39. Upon further movement (FIG. 9b), the elastic arm 64 deforms due to a contrary force exerted by a spring 70, and eventually the lever 60 snaps past the elastic arm 64 (FIG. 9c), allowing the spring 70 to move the gate element rapidly into a closed position. Thus, an injection effect can be achieved. After moving the needle out of the skin, the spring 68 moves the contact element 32 back into its starting position (FIG. 9e, a). During this movement, the lever 60 rotates twice, first in a clockwise direction (direction 72) and then in a counter clockwise direction (FIG. 9d, e), in order to move past the elastic arm 64.

Figure 7:
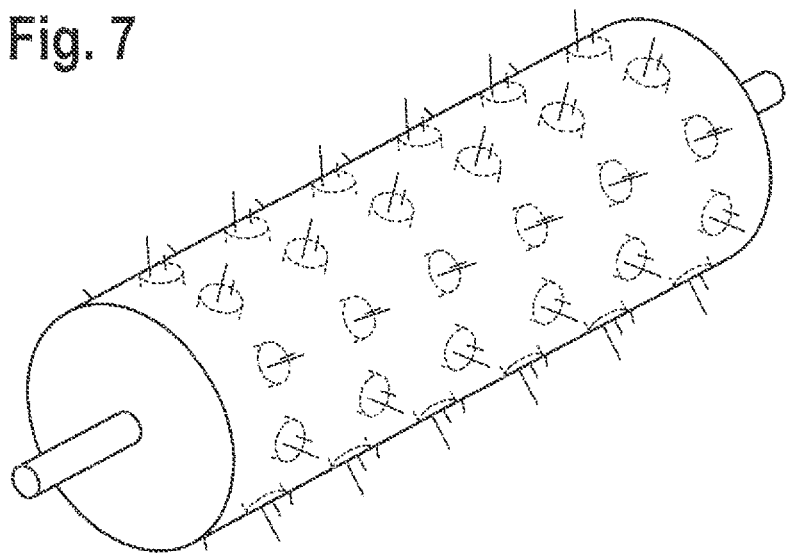
FIG. 7 shows a third embodiment.

In another variation, rather than having the solution occupy the whole inside of the roller, which costs more, an annular space can be created that occupies only the an area adjacent the needles (FIG. 7). If desired the solution inside the roller can be kept at elevated pressure by using a power source, a loaded spring or by making the reservoir or the roller from an elastic material, to assure that the roller can be held in any way, without relying on gravity.

Figure 8:
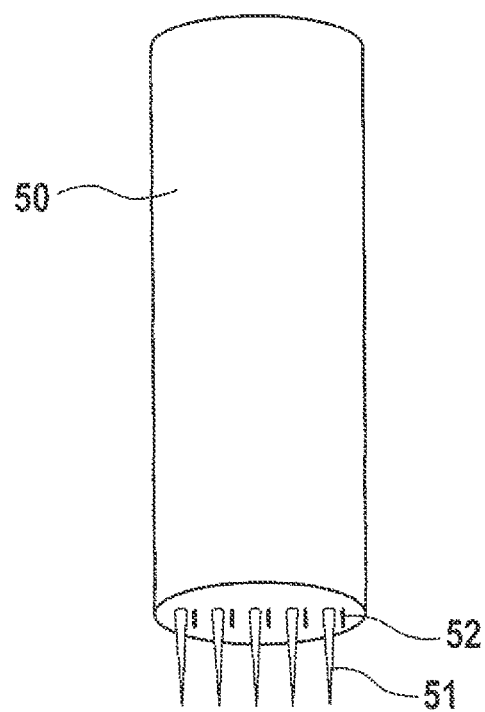
FIG. 8 shows a fourth embodiment.

In another variation, rather than having a cylindrical roller device carrying the needles, a stamp like device can be used to deliver the drug, as shown in FIG. 8. The stamper device is comprised of a longitudinal compartment 50 housing a drug, ending at a distal end (the end further from the injectors hand) in a plurality of needles 51 mounted on the distal end of the compartment. Adjacent the needles are projecting arms 52 that work in the same way as the arms 32 work in the roller device (FIG. 4). Once the stamper is pressed against the skin the arms are activated opening the outlets and delivering the drug into the skin. The stamper is more useful in tiny and hidden areas where the roller device cannot easily reach.

In all mentioned embodiments, the solution can contain any drug. A solution vehicle is preferred more than creams or ointments which are designed to facilitate the absorption of the active ingredients. Therefore, many of the preservatives and additives used in creams or ointments won't be necessary if the roller is used cutting down on cost and the potential lowered efficacy from such chemicals on the active ingredient. Moreover, since the treatment is fractionated (only part of the skin is treated with each stroke with the surrounding skin intact) stronger burning or caustic irritating drugs such as 5 Fluorouracil or topical/photodynamic therapy can be used with these devices. An example of such drug is corticosteroids. Rather than using a conventional needle to cover areas of alopecia areata, for instance, the treatment can be accomplished in much less time with a precise depth.

Chemical peels can be also administered to effect a controlled fractioned treatment with less chance for scarring and pigmentary changes since only part of the skin is treated. An additional feature with the roller device is that upper layer of the skin (epidermis) can be bypassed if desired in cases where severe discoloration is anticipated as the case with darker skin or if the target level is below the epidermis. In all, fractionated treatment and bypassing the epidermis will lead to a less eventful chemical peel treatment with less downtime and almost the same results with a classical peel that incorporates passing a gauze onto the skin with uneven pressing and uneven volume of peel administered per area. All embodiments harmonizes the delivery of chemical peel and standardizes the treatment with less chance for unpredictable results that vary with doctors performance even in the subsequent patient visits. With the fractionated roller delivery, higher concentrations of any drug or chemical peel can be given with a wider safety margin. Another useful application of all embodiments is the injection of fillers. These are substances used to correct defects, treat wrinkles and augment parts of the skin such as the cheeks and lips. A major drawback of using conventional needles in filler treatment is that the depth of injection can not be reliably and given with each stroke. Misplacement of filler may have dire consequences such as a bumpy look or rapid clearance. Yet another use of all embodiments is the use of Botox for various indications such as wrinkles and hyperhydrosis. For example in cases of hyperhydrosis using any of the embodiments would cut the duration of treatment dramatically and assure proper placement of the drug at the correct depth.

The depth of the treatment is dictated by the length of the needle. If the target is epidermis or dermis shorter needles ranging from 0.1 cm to 2 cm are used. If however fat is the target tissue longer needles up to 3 cm or longer can be used. The volume injected with each needles single stroke can be also varied with the size of the needle, the size of the engagement of the receptor and guard in the roller device and the switch spring mechanism in the roller device or the spring in the first embodiment.

Although the embodiments depict easy to use, mainly disposable devices, automated devices incorporating power sources to control various aspects in the embodiment can be employed. For example the amount of fluid dispensed per stroke can be controlled electronically by narrowing or widening the perforations the first embossment or the gates the last embodiment. The switches can be coupled to an optical or electrical sensor that opens and closes the gate elements without arms or springs.

The device can be used in both clinic and home based by patients (for shorter needles). The roller can be used after resterilization. By using the device at home, the patient can install the drug that is prescribed for him inside the device and simply use it with or without numbing creams. And additional bonus is that the roller device will induce wounds that rejuvenates the skin and helps in reducing wrinkles, color changes and possibly the risk for skin cancer. Longer needles (1.5 cm and more) are only used under a doctor's guide.

For the sake of lipolysis longer needles can be used and the roller is moved smoothly into curved surfaces with less chance for contour irregularities and a much faster treatment.

Pouring the solution onto the skin and using a regular dermaroller device will not be sufficient, even though the needle gets some fluid around its tip, the needle may be uncoated when it is urged into the skin thus reaching its target with no or very little solution. Another mechanism that prevents the topical solution from reaching down is that tissue tends to coagulate and fill with fluid and blood before the solution on the skin can reach down through these already tiny holes.

In a variation of the roller device, needles that have multiple holes along the length of the lumen of the needle can be used to deliver the solution to multiple levels of the skin simultaneously.

The reservoir is where any type of solution is stored prior to treatment. This reservoir can be disconnectable from the needle carrier, so that the operator need not to transfer the solution from a container to the reservoir but rather is ready for use once this reservoir has been connected to the device.

LIST OF NUMERALS

2 needle carrier
2*a* axis of rotation
4 outer surface
6 needle
10 compartment
11 handle
12 perforation
13 cut
14 outlet
16 slider (gate element)
18 spring
22 needle
22*a* tip
29 inside wall
33 head
39 seat
40 gate element
50 compartment
51 needles
52 arms
60 lever
60*a* first end
60*b* second end
62 pivot
64 elastic arm
66 direction
68 spring
70 spring

The invention claimed is:

1. An apparatus for transdermal or subcutaneous delivery of a bioactive solution, including a plurality of needles fixed on a needle carrier in a spaced apart relationship and projecting from the needle carrier, each needle having a tip zone adapted to receive an amount of bioactive solution from a reservoir coupled to and located above the needle carrier and to deliver the bioactive solution upon penetrating a skin;

wherein the needle carrier has a cambered surface on which the needles are fixed;

wherein the needle carrier is a rolling body rotatably supported on a handle, the rolling body carrying the needles on an outer surface in a radially projecting arrangement;

wherein the reservoir is disposed outside of and adjacent to the needle carrier and has one or more outlet device (s), each outlet device being fixed to a wall of the reservoir and being configured to sequentially cooperate with a plurality of needles arranged in a row when the needle carrier is rotated, whereby the tip zone of each needle receives an amount of bioactive solution; and wherein each outlet device comprises a gate element fixed to the wall of the reservoir and being operable by each needle in turn upon rotation of the rolling body, the gate element being configured to be opened upon approach of a needle and allowing delivery of bioactive solution from the reservoir to the tip zone of the needle, and being closed upon further movement of the needle away from the gate element.

2. The apparatus as claimed in claim 1, wherein the gate element is biased towards a closed position by a spring.

3. The apparatus as claimed in claim 1, wherein the reservoir is pressurized.

4. The apparatus as claimed in claim 1, characterized in that the reservoir is separable from the needle carrier.

5. A method of subcutaneously or transdermally delivering a bioactive solution, by using an apparatus as claimed in claim 1, applying or rolling the apparatus on the skin, thereby delivering an amount of solution each time a needle penetrates the skin.

* * * * *